(12) United States Patent
Addison

(10) Patent No.: US 8,097,272 B2
(45) Date of Patent: Jan. 17, 2012

(54) LAYERED MATERIALS FOR USE AS WOUND DRESSINGS

(75) Inventor: Deborah Addison, Lancaster (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 2538 days.

(21) Appl. No.: 10/445,222

(22) Filed: May 27, 2003

(65) Prior Publication Data

US 2010/0198127 A1    Aug. 5, 2010

Related U.S. Application Data

(63) Continuation of application No. PCT/GB01/05409, filed on Dec. 6, 2001.

(30) Foreign Application Priority Data

Dec. 7, 2000  (GB) .................................. 0029918.0

(51) Int. Cl.
*A61F 13/00* (2006.01)
*A61K 9/70* (2006.01)
*A61L 15/00* (2006.01)

(52) U.S. Cl. ............ 424/443; 424/445; 602/41; 602/46; 602/48

(58) Field of Classification Search .............. 602/41–43, 602/46, 48; 424/443, 445–447
See application file for complete search history.

(56) References Cited

U.S. PATENT DOCUMENTS

| | | | |
|---|---|---|---|
| 4,668,564 A | 5/1987 | Orchard | |
| 4,743,499 A | 5/1988 | Volke | |
| 5,112,618 A | 5/1992 | Cartmell et al. | |
| 5,160,328 A | 11/1992 | Cartmell et al. | |
| 5,204,110 A * | 4/1993 | Cartmell et al. | 424/443 |
| 5,328,450 A * | 7/1994 | Smith et al. | 602/59 |
| 5,356,372 A | 10/1994 | Donovan et al. | |
| 5,480,377 A * | 1/1996 | Cartmell et al. | 602/48 |
| 5,501,661 A | 3/1996 | Cartmell et al. | |
| 5,571,529 A * | 11/1996 | Cheong | 424/445 |
| 5,643,187 A * | 7/1997 | Naestoft et al. | 602/43 |
| 5,928,174 A * | 7/1999 | Gibbins | 602/41 |
| 5,976,117 A * | 11/1999 | Dunshee et al. | 604/307 |

FOREIGN PATENT DOCUMENTS

| | | |
|---|---|---|
| EP | 0 190 814 A2 | 8/1986 |
| EP | 0 301 753 A2 | 2/1989 |
| EP | 0 541 391 A1 | 5/1993 |
| EP | 0 604 103 A1 | 6/1994 |
| EP | 1 658 865 A1 | 5/2006 |
| GB | 2 290 031 A | 12/1995 |
| GB | 2 410 748 A | 8/2005 |
| GB | 2 428 581 A | 2/2007 |
| GB | 2 433 263 A | 6/2007 |
| JP | 04-073011 | 3/1992 |
| WO | 03/051409 A1 | 6/2003 |
| WO | 03/066116 A1 | 8/2003 |
| WO | 03/092756 A1 | 11/2003 |
| WO | 2005/075001 A1 | 8/2005 |
| WO | 2007/113453 A1 | 10/2007 |
| WO | 2008/055586 A1 | 5/2008 |
| WO | 2010/000450 A2 | 1/2010 |
| WO | 2010/089546 A2 | 8/2010 |
| WO | 2011/058311 A1 | 5/2011 |

* cited by examiner

*Primary Examiner* — Patricia Bianco
*Assistant Examiner* — Keri J Nelson
(74) *Attorney, Agent, or Firm* — Morgan, Lewis & Bockius LLP

(57) ABSTRACT

The invention provides a wound dressing comprising a layered material comprising a hydrophilic foam layer formed from a first polyurethane and a hydrogel layer formed from a second polyurethane, wherein the hydrogel layer is laminated to the hydrophilic foam layer. The invention also provides methods for preparing the same.

16 Claims, 1 Drawing Sheet

LAYERED MATERIALS FOR USE AS WOUND DRESSINGS

CROSS-REFERENCE TO RELATED APPLICATIONS

Figure 1:
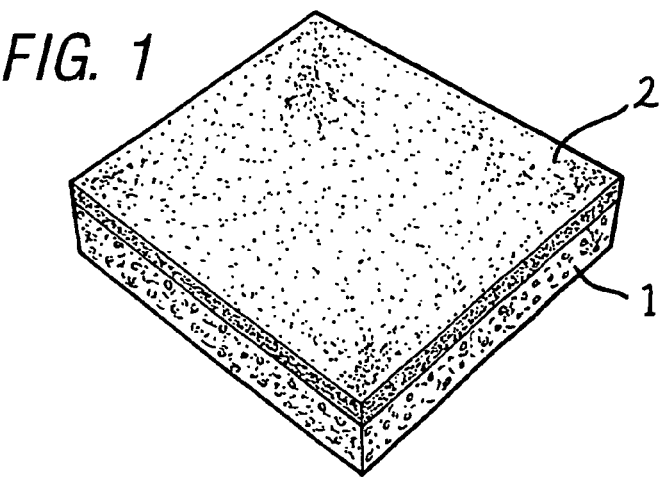

This application is a continuation of application PCT/GB01/05409 filed on Dec. 6,2001, which claims foreign priority to GB application 0029918.0 filed on Dec. 7,2000, the complete disclosures of which are hereby incorporated herein by reference for all purposes.

The present invention relates to layered polyurethane materials and the use thereof as wound dressings.

EP-A-0541391 describes hydrophilic polyurethane foams for use as absorbent and wound contacting layers in wound dressings.

It is also known to provide wound dressings in which the wound contacting layer comprises a polyurethane hydrogel material especially suitable for absorbing bodily fluids such as wound exudate. For example, U.S. Pat. No. 5,160,328 describes such a dressing having a wound contacting polyurethane hydrogel layer. The polyurethane gel comprises from 0% to 90% of polyhydric alcohol such as polypropylene glycol, from 6% to 60% by weight of an isocyanate-terminated prepolymer, from 4% to 40% by weight of a polyethylene oxide based diamine, and the balance water. The hydrogel layer is disposed on a support layer that provides mechanical support for the relatively weak hydrogel.

Hydrogel dressings are advantageous because wound exudate does not generally dry and consolidate with hydrogels. Consequently, the removal of a hydrogel dressing is usually neither painful nor detrimental to the healing process. Hydrogel dressings are particularly desirable for the treatment of burns.

Unfortunately, hydrogel dressings have limited capacity to absorb further water. Furthermore, there are difficulties in handling the structurally weak gels in high speed manufacturing processes. This has been addressed in U.S. Pat. No. 5,160,328 by the provision of a support layer underneath the hydrogel layer, but it is difficult to achieve satisfactory adhesion of the hydrogel layer to the support layer.

EP-A-0610056 describes a hydrogel dressing which comprises a wound contacting layer of hydrogel in face-to-face relationship with a substrate. The hydrogel facing surface of the substrate comprises fibers projecting into the hydrogel. The hydrogel is cross-linked on the substrate and thereby firmly anchored thereto. The preferred hydrogel for use in this invention is polyvinylpyrrolidone, which is cross-linked by irradiation.

EP-A-0604103 describes processes by which a polymeric hydrogel can be securely adhered to a substrate to form a hydrogel laminate with greatly improved delamination resistance. The laminate is formed by casting onto a polymeric adhesive-coated substrate an aqueous solution of hydrophilic polymer, then exposing this composite to ionizing radiation which cross-links the hydrophilic polymer to form a hydrogel and also induces copolymerisation of the hydrophilic polymer and the adhesive polymer.

U.S. Pat. No. 4,668,564 describes layered materials for use as a hot or cold compress. The materials comprise a layer of substituted urea/urethane hydrogel material bonded to a porous substrate.

It has now been found that novel composite polyurethane structures provide a hydrogel layer with enhanced rigidity, delamination resistance and liquid absorbency.

The present invention provides a wound dressing comprising a layered material comprising a hydrophilic foam layer formed from a first polyurethane and a hydrogel layer formed from a second polyurethane, wherein the hydrogel layer is laminated to the hydrophilic foam layer.

Preferably, the hydrophilic foam layer has a density of from 0.28 to 0.5 g/cm$^3$, and more preferably from 0.32 to 0.48 g/cm$^3$. Preferably, the foam has an elongation to break of at least 150%, more preferably from 500% to 1000%. The foam is hydrophilic and absorbs aqueous fluids such as wound exudate with swelling. However, the foam is preferably highly cross-linked and substantially insoluble in water. Preferably, the foam has an absorbency of at least 3 g saline/g, and preferably a swellability in water of at least 200%. Preferably, the hydrophilic foam is a foam as described in EP-A-0541391, the entire content of which is incorporated herein by reference.

Preferably, the foamed polyurethane layer comprises less than 10% water prior to use as an absorbent, more preferably less than 5% water and more preferably it contains less than 2% of water before use.

The hydrophilic foam provides enhanced absorbency for liquid exudate. This is because the initial substantially anhydrous condition and porous structure of the foam enable it to absorb a larger amount of water by both chemical and physical absorption that is the case for the corresponding hydrogel material. Furthermore, the porous structure of the foam provides for rapid uptake of liquid exudate, in contrast to pure hydrogel dressings. Preferably, the hydrophilic foam layer has a thickness of from 1 to 20 mm, more preferably from 1.5 to 5 mm.

The hydrogel layer is formed from a polyurethane that entraps water to form a gel. Preferably, the hydrogel layer is substantially continuous, and preferably it is substantially non-porous. Preferably, the density of the hydrogel layer is greater than 0.5 g/cm$^3$, more preferably greater than 0.8 g/cm$^3$, and most preferably from 0.9 to 1.1 g/cm$^3$. Preferably, the thickness of the hydrogel layer is from 1 mm to 10 mm, more preferably from 2 mm to 5 mm. In an embodiment, the hydrogel layer is substantially unfoamed.

Preferably, the polyurethane of the hydrogel layer is cross-linked and preferably it is substantially insoluble in water at ambient temperature. However, the structure of the hydrogel layer absorbs and entraps water to provide a highly hydrated gel structure in contrast to the porous foam structure of the foam layer. Preferably, the gel can absorb 1 to 10 g/g of physiological saline at 20°, more preferably 2 to 5 g/g. The saline absorbency is determined by the steps of: weighing the hydrogel, submerging the hydrogel in 0.9% saline for 24 hours, draining for 30 seconds, and reweighing.

Preferably, the dry weight of the hydrogel layer is from 1000 to 5000 g/m$^2$, more preferably from 2000 to 4000 g/m$^2$. Preferably, the hydrogel comprises from 1 to 30% of water, more preferably from 10 to 20% by weight of water before use. Preferably, the hydrogel contains from 1 to 40%, more preferably from 5 to 15%, by weight of one or more humectants, preferably selected from the group consisting of glycerol, propylene glycol, sorbitol, mannitol, polydextrose, sodium pyrrolidine carboxylic acid (NaPCA), hyaluronic acid, aloe, jojoba, lactic acid, urea, gelatin, lecithin and mixtures thereof. The entrapped water and optional humectants give the hydrogel a soft, moist wound-friendly surface for contacting the wound.

The hydrogel layer is laminated to the foam layer. That is to say, it is applied to and at least partially covers one surface of the foam layer. Preferably, the hydrogel layer is bonded to the foam layer, for example by an adhesive or by radiation cross-linking. More preferably, the hydrogel layer is bonded to the foam layer by urethane or urea linkages. This can be achieved easily by applying the foam layer to the hydrogel layer (substantially without mixing) before polyurethane curing is complete, as described in more detail below.

Preferably, the foam layer polyurethane and/or the hydrogel layer polyurethane are formed by crosslinking an isocyanate-capped prepolymer. Preferably, the prepolymer is the same for both layers. Preferably, the prepolymer comprises an isocyanate-capped polyether prepolymer, and more preferably it comprises an isocyanate-capped ethyleneoxy/propyleneoxy prepolymer. For example, one of the prepolymers available under the Registered Trade Mark HYPOL from Dow Chemical Company, 2 Heathrow Boulevard, 284 Bath Road, West Drayton, UK.

Preferably, the foam layer and/or the hydrogel layer contains a medicament. Suitable medicaments include antiseptics such as silver sulfadiazine, chlorhexidine, triclosan or povidone iodine, analgesics, steroids, antibiotics, growth factors or mixtures thereof. Preferably, the layered material is substantially sterile.

Preferably, the wound dressing further comprises a liquid-impermeable backing sheet extending over the laminated material. Preferably, the backing sheet is a semipermeable sheet, for example a sheet of a microporous polyurethane foam such as ESTANE (Registered Trade Mark). Preferably, the backing sheet is provided with a continuous or interrupted layer of a pressure-sensitive adhesive, preferably one of the known medical-grade adhesives. Preferably, an adhesive-coated margin of the backing sheet extends beyond at least one edge of the laminated material for attachment of the backing sheet to the skin of a patient adjacent to a wound under treatment. More preferably, an adhesive-coated margin of the backing sheet extends around all edges of the layered material so as to provide a so-called island dressing.

The backing sheet may be provided on either the foam side of the layered material or on the hydrogel side. Intermediate layers, such as absorbent layers or support layers, may be provided between the layered material and the backing sheet.

The layered material may be provided in substantially flat sheet form for topical application to wounds. However, the layered material may be contoured for application to body surfaces having high curvature. In certain preferred embodiments the layered material is formed into a three-dimensional shape for deep cavity wound filling. For example, the layered material may be folded or crumpled. Preferably, a cavity wound dressing comprises one or more elongated strips of the layered material, which may be folded or entangled or coiled, and in certain embodiments the cavity dressing comprises a plurality of entangled strips of the layered material.

The present invention further provides the use of a wound dressing layered material according to the invention for the preparation of a dressing for use in the treatment of wounds. Preferably, the dressing is in accordance with one of the above-described embodiments In a further aspect, the present invention provides a method of treatment of a wound comprising applying a wound dressing according to the present invention to the surface of the wound with the foam layer or the hydrogel layer of the layered material in liquid communication with the wound, and preferably in contact with the wound, to absorb wound exudate.

The present invention further provides a method of preparing a layered structure for use as a cavity wound dressing comprising the steps of: providing a first, foamed polyurethane layer by reacting an isocyanate-capped prepolymer with water and optionally one or more compounds selected from polyurethane chain extending or terminating compounds other than water and catalysts for the polymerisation of isocyanate; providing a second, hydrogel polyurethane layer by reacting an isocyanate-containing prepolymer with one or more compounds selected from water, other polyurethane chain extending or terminating compounds and catalysts for the polymerisation of isocyanate; laminating the second layer to the first layer; curing and drying the polyurethane layers to provide the layered material, wherein the method further comprises slitting the layered material before said step of curing and drying is complete.

Preferably, the step of slitting comprises slitting the layered material into a plurality of connected strips.

Preferably, the layered structure prepared by the method of the invention is a layered structure according to the invention as hereinbefore described. Preferably, the first layer is laminated to the second layer before the steps of reacting are complete, whereby urethane or urea linkages are formed between the foamed polyurethane layer and the hydrogel polyurethane layer.

Preferably, the prepolymer is the same for both layers. Preferably, the prepolymer comprises an isocyanate-capped polyether prepolymer, and more preferably it comprises an isocyanate-capped ethyleneoxy/propyleneoxy prepolymer. For example, one of the prepolymers available under the Registered Trade Mark HYPOL from Dow Chemical Company, 2 Heathrow Boulevard, 284 Bath Road, West Drayton, UK.

Preferably, the chain terminating compounds comprise a monoamine or a monohydric alcohol, more preferably a $C_1$ to $C_3$ alcohol, and most preferably methanol. In certain preferred embodiments of the foam preparation, one part of the prepolymer is reacted with water in the presence of from 0.05 to 0.25 parts by weight of methanol or from 0.1 to 0.3 parts by weight of ethanol. The amounts of chain terminating compounds influence the physical properties of the polyurethane foam or gel. For example, the tackiness of the polyurethane increases with increasing monohydric alcohol or monoamine content.

Preferably, the chain extending compounds comprise water or a diamine. Reaction with water produces carbon dioxide for foaming and urethane cross-links. Reaction with diamines, which takes place much faster than reaction with water, gives urea cross-links. Preferred diamines include $C_3$ to $C_9$ alkylene diamines such as hexamethylene diamine.

Preferably, the step of providing the polyurethane foam layer comprises: mixing 1 part by weight of an isocyanate-capped prepolymer having from 0.5 to 1.2 meq NCO groups/g with from 0.4 to 1.0 parts by weight of water in the presence of from 0.05 to 0.4 parts by weight of a $C_1$ to $C_3$ monohydric alcohol.

Preferably, the method of the invention comprises the step of slitting the layered material to provide a plurality of linked strips of the layered material. As curing and drying proceeds, the strips curl and entangle as a result of differential shrinkage rates in the foam and hydrogel layers. This can result in a three-dimensional bundle of strips suitable for use as a deep cavity wound dressing.

Figure 2A:
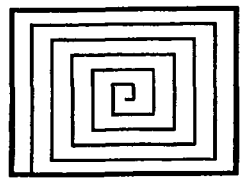
Figure 2B:
Figure 3:
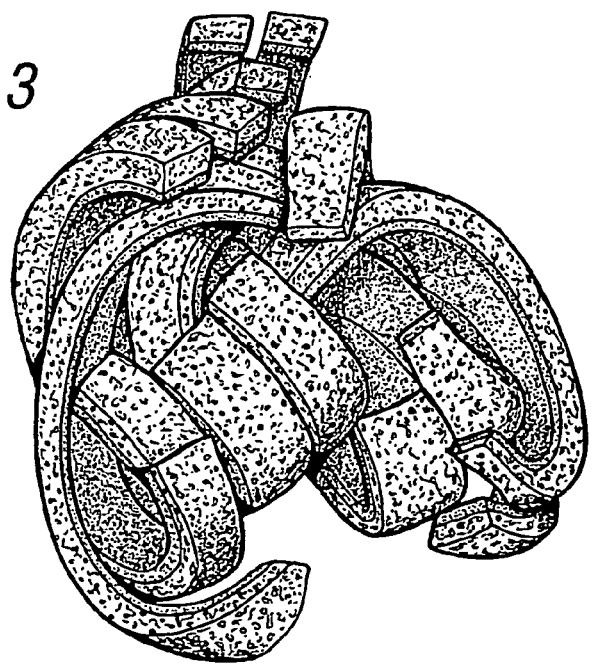

Specific embodiments of the invention will now be described further, by way of example, with reference to the accompanying drawings, in which:

FIG. 1 shows a perspective view of a flat layered material according to the present invention; and FIG. 2a and 2b show a plan view of two alternative patterns of full thickness slits formed in a laminate prior to final curing and drying in order to achieve a deep cavity dressing; and FIG. 3 shows a perspective view of a deep cavity wound dressing formed from layered material in accordance with the invention.

EXAMPLE 1

A layered material is prepared from the following constituents:

| Foam Layer: | HYPOL[a] | 50 g |
| --- | --- | --- |
| | Water | 32 g |
| | Acrylic copolymer[b] | 12 g |
| | Methanol | 6 g |
| Hydrogel Layer | HYPOL[a] | 25 g |
| | Water | 100 g |

[a]HYPOL PreMA G60 from Dow Corning Ltd.
[b]PRIMAL B-15J or RHOPLEX N-560 (Registered Trade Marks).

The components of each layer are mixed and spread individually to make flat sheets of nominal thickness 1 to 5 mm. The sheets are allowed to cure partially for about 90 seconds at ambient temperature, and are then pressed gently together and placed in an oven at 100° C. for about 15 minutes to complete the curing and drying.

The resulting laminate, which is shown in FIG. 1 has a polyurethane foam layer 1 laminated to a hydrogel wound contacting layer 2.

EXAMPLE 2

A deep cavity wound dressing is prepared as follows.

The procedure of Example 1 is followed with the additional step of slitting the laminate in dendritic or spiral fashion as shown in FIG. 2 before the final oven curing and drying step. The process includes an additional drying and curing step at 40° C. for about 30 minutes. The strands of the laminate curl and entangle during the final curing and drying step to produce the three-dimensional deep cavity dressing shown in FIG. 3.

The above embodiments have been described by way of example only. Many other embodiments falling within the scope of the accompanying claims will be apparent to the skilled reader.

The invention claimed is:

1. A wound dressing comprising: a layered material comprising a hydrophilic foam layer formed from a first polyurethane and a hydrogel layer formed from a second polyurethane, wherein the hydrogel layer is laminated to the hydrophilic foam layer and bonded to the hydrophilic foam layer by urethane or urea linkages, and wherein the wound dressing comprises one or more entangled, elongated strips of the layered material forming a bundle suitable for cavity wound filling.

2. The wound dressing according to claim 1, wherein the hydrophilic foam layer has a density of from 0.28 to 0.5 g/cm$^3$.

3. The wound dressing according to claim 1, wherein the hydrophilic foam layer has a thickness of from 1 to 20 mm.

4. The wound dressing according to claim 1, wherein the hydrogel layer is substantially unfoamed.

5. The wound dressing according to claim 1, wherein the dry weight of the hydrogel layer is from 1000 to 5000 g/m$^2$.

6. The wound dressing according to claim 1, wherein the foam layer polyurethane and/or the hydrogel layer polyurethane are formed by crosslinking an isocyanate-capped prepolymer.

7. The wound dressing according to claim 6, wherein the prepolymer comprises an isocyanate-capped polyether prepolymer.

8. The wound dressing according to claim 7, wherein the prepolymer comprises an isocyanate-capped ethyleneoxy/propyleneoxy prepolymer.

9. A wound dressing according to any preceding claim wherein the hydrogel layer comprises from 10 to 30% by weight of water and the foam layer comprises less than 10% by weight of water.

10. A wound dressing according to claim 1, which is substantially sterile.

11. A wound dressing according to claim 1, wherein the foam layer and/or the hydrogel layer contains a medicament.

12. A wound dressing according to claim 1, further comprising a liquid-impermeable backing sheet extending over the laminated material.

13. A wound dressing according to claim 1, wherein the layered material is folded or crumpled into a three-dimensional shape for cavity wound filling.

14. A method of treatment of a wound comprising applying the wound dressing of claim 1 to the surface of a wound, wherein either the foam layer or the hydrogel layer of the layered material is in liquid communication with the wound to absorb wound exudate.

15. A method of preparing a layered structure for use as a cavity wound dressing comprising the steps of: providing a first, foamed polyurethane layer by reacting an isocyanate-capped prepolymer with water and optionally one or more compounds selected from polyurethane chain extending or terminating compounds other than water and catalysts for the polymerisation of isocyanate; providing a second, hydrogel polyurethane layer by reacting an isocyanate-containing prepolymer with one or more compounds selected from water, other polyurethane chain extending or terminating compounds and catalysts for the polymerisation of isocyanate; laminating the second layer to the first layer; and curing and drying the polyurethane layers to provide the layered material, wherein the method further comprises slitting the layered material before said step of curing and drying is complete.

16. A method according to claim 15, wherein said step of slitting comprises slitting the layered material into a plurality of connected strips.

* * * * *